United States Patent [19]

Bethune et al.

[11] Patent Number: 5,226,416

[45] Date of Patent: Jul. 13, 1993

[54] MONITORING AND ALARM APPARATUS

[75] Inventors: Donald W. Bethune; Michael L. Swain, both of Cambridgeshire, United Kingdom

[73] Assignee: Pneu Pac Limited, Hertfordshire, United Kingdom

[21] Appl. No.: 623,732

[22] PCT Filed: Jun. 13, 1989

[86] PCT No.: PCT/GB89/00656

§ 371 Date: Dec. 14, 1990

§ 102(e) Date: Dec. 14, 1990

[87] PCT Pub. No.: WO89/12420

PCT Pub. Date: Dec. 28, 1989

[30] Foreign Application Priority Data

Jun. 16, 1988 [GB] United Kingdom ............... 8814291

[51] Int. Cl.$^5$ ............................................. A61B 5/00
[52] U.S. Cl. ................................. 128/630; 128/725; 128/716; 340/573
[58] Field of Search .............. 128/202.22, 716, 718, 128/719, 720, 721, 670, 671, 630, 668; 340/573

[56] References Cited

U.S. PATENT DOCUMENTS

| | | | |
|---|---|---|---|
| 3,498,287 | 3/1970 | Ertl | 128/731 |
| 3,618,592 | 11/1971 | Stewert | 128/2.06 |
| 3,948,250 | 4/1976 | Weisman | 128/2.05 |
| 4,197,854 | 4/1980 | Kasa | 128/630 |
| 4,365,636 | 12/1982 | Barker | 128/716 |
| 4,387,722 | 6/1983 | Kearns | 128/716 |
| 4,403,215 | 9/1983 | Hofmann et al. | 340/573 |
| 4,546,770 | 10/1985 | Schlessinger et al. | 128/630 |
| 4,550,726 | 11/1985 | McEwen | 128/202.22 |
| 4,630,614 | 12/1986 | Atlas | 128/721 |
| 4,813,427 | 3/1989 | Schlaefke | 128/721 |
| 4,819,860 | 4/1989 | Hargrove et al. | 128/668 |

FOREIGN PATENT DOCUMENTS 2082328 3/1982 United Kingdom ............... 128/720

OTHER PUBLICATIONS

*Microprocessor-Based Home Monitor for Sudden Infant Death Syndrome*, Kejariwal et al, 1986, pp. 51-54, Proceedings of the 12th Annual Northeast Bioengineering Conference.

Primary Examiner—Ruth S. Smith
Assistant Examiner—Robert L. Nasser, Jr.
Attorney, Agent, or Firm—Young & Thompson

[57] ABSTRACT

This invention relates to apparatus for monitoring output signals from a sensor. Apparatus (17) monitors signals from sensors (10 to 12). A C.P.U. (18) in the apparatus (17) provides warning signals if the output of a sensor breaches an alarm band or band set by the C.P.U. in response to the initial values of the sensor output.

11 Claims, 2 Drawing Sheets

MONITORING AND ALARM APPARATUS

This invention relates to apparatus for monitoring output signals from a sensor and in particular, but not exclusively, for monitoring signals from sensors which detect physiological conditions of patients in intensive care.

With the increase in technology associated with the treatment of very seriously ill patients, wards and operating theatres are now becoming full of various types of monitoring equipment which require the nursing or medical staff to set alarm levesl in accordance with the device and the health of the patient. Generally only single alarm levels are available and so only crisis alarm levels can be set. Frequently these alarms can be switched off to enable staff to fit a device onto a patient or take it from him, and because the operation is entirely manual they are often not switched back on.

From one aspect the invention consists in an apparatus for monitoring output signals from a sensor, comprising an input for receiving the signals, means for automatically setting upper and lower levels to define a band around the initial value or values of the signals and means for indicating when the value of the signals passes through a particular level.

Thus with the applicants' apparatus the alarm level or levels are selected automatically by the initial output of the sensor.

In a preferred embodiment the level setting means defines a plurality of bands having levels of increasing deviation from the initial values and the indicating means may provide an indication which is representative of the level of greatest deviation passed through by the signal. Thus there may be different combinations of visual and audible alarms according to the level reached by the signal.

The levels may be set as predetermined percentage deviations from the initial values in which case the apparatus may further comprise means for comparing the initial values or the set levels with predetermined parameters and means for indicating if the initial values or the set levels are abnormal or unacceptable.

The apparatus may include means for manually overriding the indicating means, in which case it is preferred that the apparatus further includes automatic reset means for resetting the indicating means a predetermined period after the actuation of the override means. In addition the apparatus may include a further means for manually cancelling the indicating means, in which case a non-fluctuating signal will not cause an alarm situation. When a varying signal is received the signal levels will be monitored and the alarm level will again be automatically selected.

The apparatus may further comprise inputs for a plurality of sensors in which case the level setting means may set levels for the signals on each input.

From a further aspect the invention consists in a device for monitoring output signals from a sensor, comprising an input for receiving the signals and means for setting an alarm level in dependence on the initial value or values of the signals.

In any of the above cases the level setting means may sample the signal over a predetermined period to obtain an initial value, for example it may sample the peaks and troughs of the signal.

For the purposes of this specification the term "value of the signal" incorporates any appropriate measurable characteristic of the signal, for example its amplitude, frequency or phase, or a combination of any of these.

Although the invention has been defined above it is to be understood it includes any inventive combination of the features set out above or in the following description.

The invention may be performed in various ways and a specific embodiment will now be described, by way of example, with reference to the accompanying drawings, in which.

Figure 2:
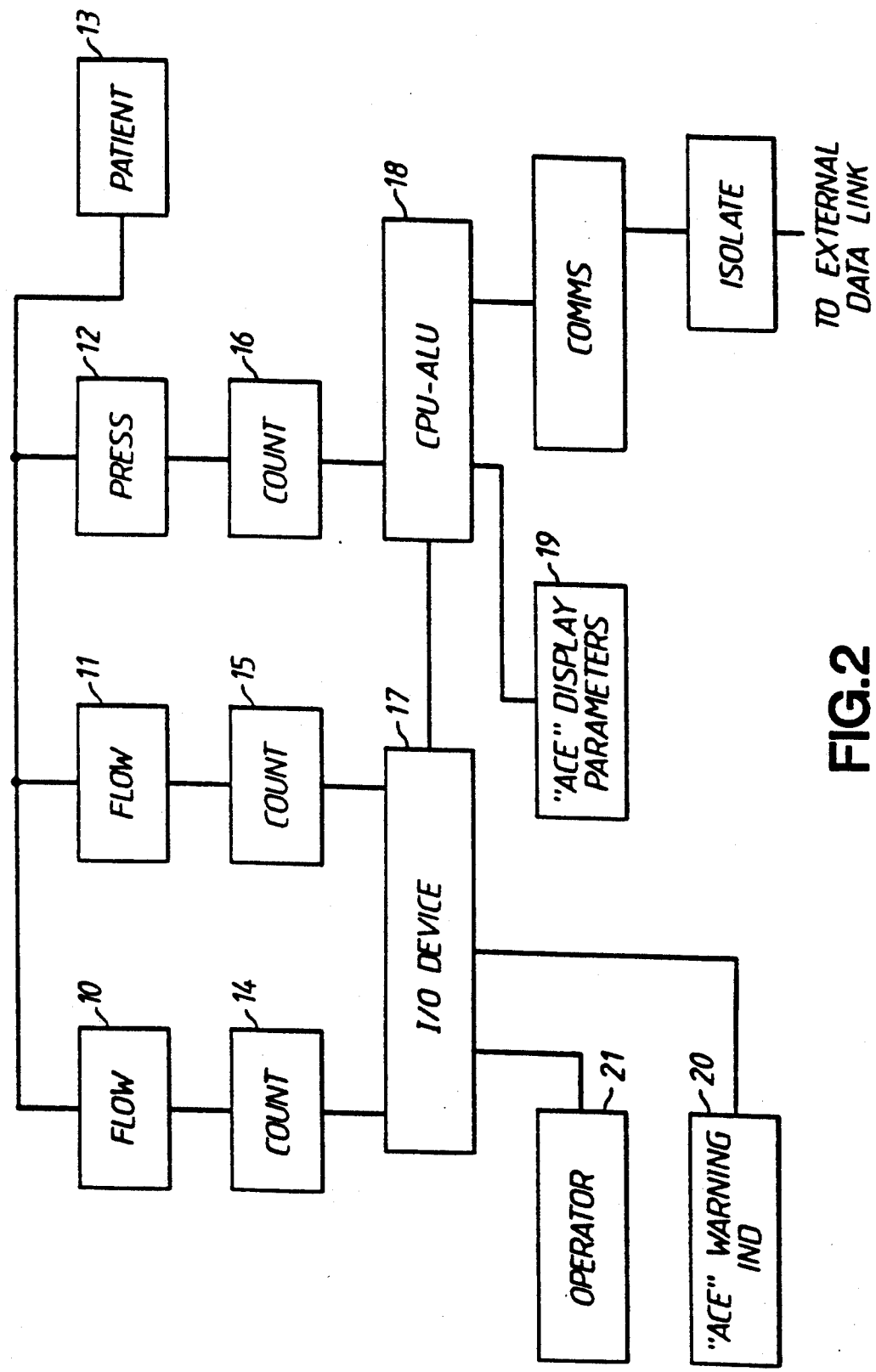
FIG. 2 is a schematic diagram of a ventilator monitor incorporating the apparatus.

For convenience the specific embodiment of the invention will be described in connection with a ventilation monitor of the type shown in FIG. 2. Here it will be seen that sensors 10 to 12 monitor the inspiratory flow, the expiratory flow and the pressure of a patient 13's breath and produces output signals via analog-to-digital converters 14 to 16. These signals are fed to monitoring apparatus generally indicated at 17.

The apparatus 17 has a central processing unit 18 which is responsive to the outputs of the sensors 10 to 12 to display apparatus conditions on a display 19, to provide warning indications on an indicator 20 and to respond to operator control via a switch 21.

Figure 1:
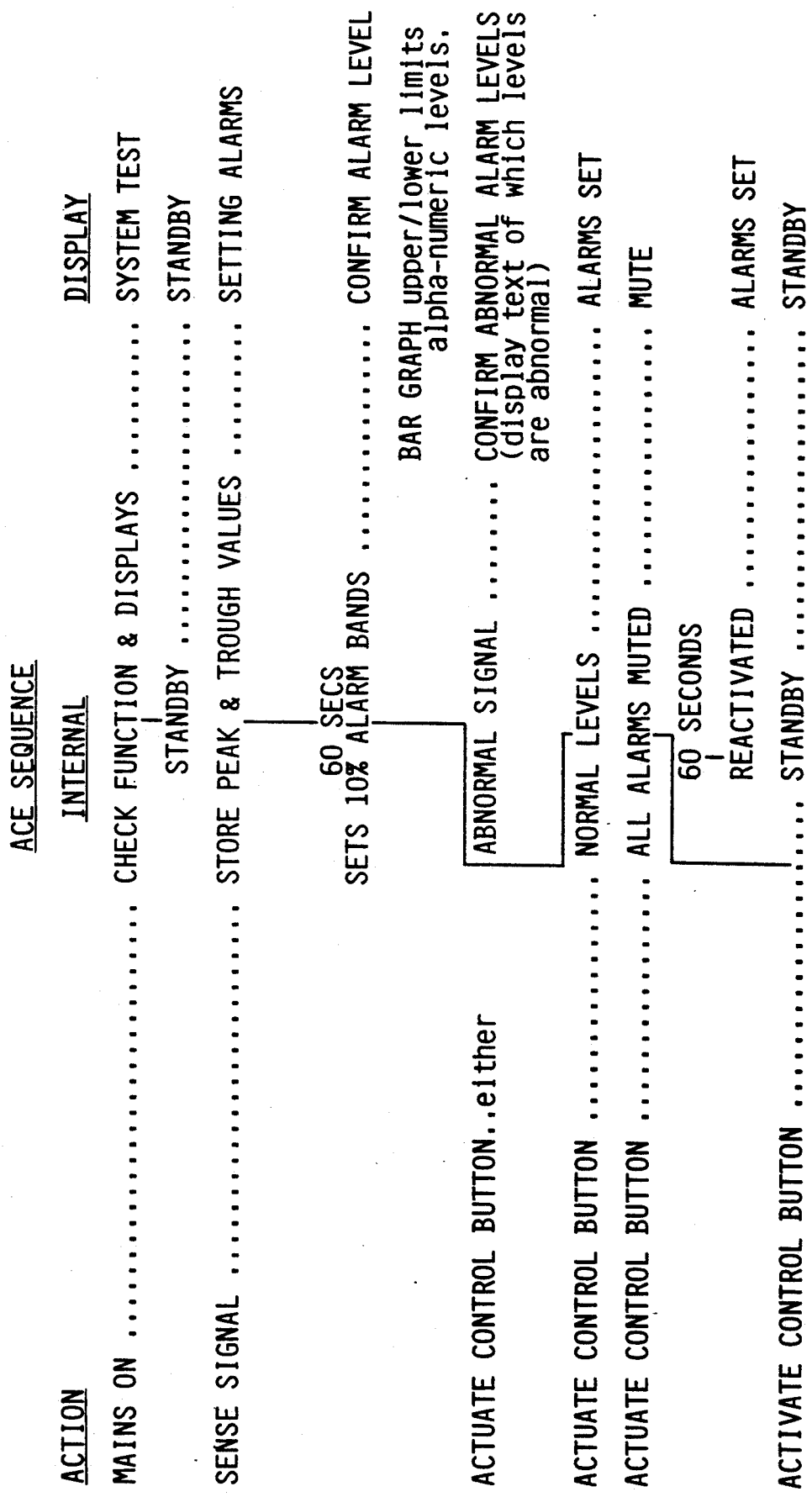
FIG. 1 shows an operational sequence of a monitoring apparatus.

Thus as can be seen from FIG. 1 an operator initiates the monitoring of the sensors 10 to 12 by switching on apparatus 17 which causes the CPU 18 to carry out internal checks which once complete produce a standby report on the display 19. The sensors are then connected to the apparatus 17 and on receipt of signals from them the apparatus 17 monitors those signals to obtain an initial value, for example the initial peak and trough values. It then calculates different levels so as to set alarm bands around the initial values received from the patient. Conveniently these will be 10% bands.

For example, in the case of an inspiratory ventilator pressure of 20 cms WG the level should be at 22, 24 and 26 cms WG for over-pressure, and at 18, 16 and 14 cms WG for cycling pressure. In that case a peak inspiratory pressure between 22 and 24, or between 16 and 18, would activate a low level visual and auditory prompt on the indicator 20. A greater deviation of 20% would activate a cautionary prompt and if the deviation exceeded 30%, i.e. over 26 or not reaching 14 cms WG there would be both visual and auditory alarm signals.

In some situations the 10% bands would be inappropriate, for example if the patient was hardly breathing when first attached to the monitor, or with certain types of parameters such as expiratory pressure, which is normally zero. The central processing unit can be set up to be aware of the conditions where 10% banding is not appropriate and either provide preset banding or banding on a different percentage basis. Additionally, or alternatively, it may simply indicate that the alarms levels set are abnormal in accordance with predetermined parameters held within the CPU.

The apparatus may further display the actual measured values either in the form of bar graphs or alphanumerically and it may indicate some or all of the levels which have been set.

As indicated in FIG. 1 once the levels have been set the apparatus either displays that fact or the existence of an abnormal alarm level. Following actuation of the control button or switch 21 the apparatus then proceeds to monitor the patient's sensors, but if it is necessary to temporarily disconnect the patient from the sensors the alarms can be muted by further operation of the control button or switch 21. This mutes the alarms for a predetermined period, whereupon they are automatically reactivated. If the control button is reactivated within a predetermined period following the initial activation, the device is put into a standby mode and will remain there until a varying signal is received.

It will thus be appreciated that in contrast to the existing monitoring apparatus this apparatus can be switched on in standby mode for an indefinite period until the patient is connected. The subsequent selection of alarm levels is automatic and the button press will confirm the settings.

Further, the automatic setting of alarm levels of varying urgency removes the temptation for nursing staff to set the alarm levels at too great a deviation. Further the alarms cannot be muted for any significant period of time.

We claim:

1. Apparatus for monitoring output signals from a sensor, comprising an input for receiving said output signals, means for automatically setting upper and lower levels to define a band around the initial value or values of said output signals, means for comparing the levels set with predetermined parameters and for indicating whether the set levels are abnormal or unacceptable.

2. A device as claimed in claim 1 including means for manually overiding the indicating means.

3. A device as claimed in claim 2, further including automatic reset means for resetting the indicating means a predetermined period after activation of the overide.

4. A device as claimed in claim 1, wherein the indicating means provides an audible and/or visual indication.

5. A device as claimed in claim 1, further comprising inputs for receiving output signals from a plurality of sensors and wherein the level setting means sets levels for the signals on each input.

6. Apparatus for monitoring output signals from a sensor, comprising an input for receiving said output signals, means for automatically setting upper and lower levels to define a band around the initial value or values of said output signals, means for indicating when the value of said output signals passes through a particular level, means for manually canceling the indicating means such that a non-fluctuating signal will not cause an alarm signal and means for resetting the levels after cancellation in response to a fluctuating signal.

7. Apparatus for monitoring output signals from a sensor, comprising an input for receiving said output signals, means for automatically setting a plurality of bands around the initial value or values of said output signals, the bands having levels of increasing deviation from the initial value or values of said output signals, indicating means for providing, whenever said output signals pass through any level, an indication which is representative of the level of greatest deviation passed through by said output signals, and means for comparing the levels set with predetermined parameters and for indicating whether the set levels are abnormal or unacceptable.

8. Apparatus as claimed in claim 7, wherein the level setting means includes means for setting the levels as predetermined percentage deviations from the initial values.

9. Apparatus as claimed in claim 7, wherein the level setting means includes means for sampling said output signals over a predetermined period to obtain an initial value.

10. Apparatus as claimed in claim 7, wherein the level setting means includes means for sampling said output peaks and troughs of the signals to determine the initial value or values.

11. Apparatus for monitoring output signals from a sensor, comprising an input for receiving said output signals, means for automatically setting a plurality of bands around the initial value or values of said output signals, the bands having levels of increasing deviation from the initial value or values of said output signals, indicating means for providing, whenever said output signals pass through any level, an indication which is representative of the level of greatest deviation passed through by said output signals, and means for manually canceling the indicating means such that a non-fluctuating signal will not cause an alarm signal and means for resetting the levels after cancellation, in response to a fluctuating signal.

* * * * *